United States Patent
Borzilleri et al.

(10) Patent No.: US 7,470,693 B2
(45) Date of Patent: *Dec. 30, 2008

(54) OXALAMIDE DERIVATIVES AS KINASE INHIBITORS

(75) Inventors: Robert M. Borzilleri, New Hope, PA (US); Gretchen M. Schroeder, Ewing, NJ (US); Lyndon A. M. Cornelius, Jackson, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 247 days.

This patent is subject to a terminal disclaimer.

(21) Appl. No.: 11/406,795

(22) Filed: Apr. 19, 2006

(65) Prior Publication Data

US 2006/0241104 A1 Oct. 26, 2006

Related U.S. Application Data

(60) Provisional application No. 60/673,727, filed on Apr. 21, 2005.

(51) Int. Cl.
C07D 471/02 (2006.01)
A61K 31/519 (2006.01)

(52) U.S. Cl. ............... 514/258.1; 514/259.1; 514/262.1; 514/265.1; 514/300; 514/303; 544/253; 544/255; 544/262; 546/113; 546/114; 546/115; 546/118

(58) Field of Classification Search ...................... None
See application file for complete search history.

(56) References Cited

U.S. PATENT DOCUMENTS

| | | | |
|---|---|---|---|
| 6,214,344 | B1 | 4/2001 | Schwall et al. |
| 6,429,213 | B1 | 8/2002 | Xue et al. |
| 6,858,626 | B2 | 2/2005 | Xue et al. |
| 6,982,265 | B1 | 1/2006 | Hunt et al. |
| 2005/0239820 | A1 | 10/2005 | Borzilleri et al. |
| 2005/0245530 | A1 | 11/2005 | Borzilleri et al. |
| 2005/0288289 | A1 | 12/2005 | Crispino et al. |
| 2005/0288290 | A1 | 12/2005 | Borzilleri et al. |
| 2006/0004006 | A1 | 1/2006 | Borzilleri et al. |
| 2006/0009453 | A1 | 1/2006 | Geuns-Meyer et al. |

FOREIGN PATENT DOCUMENTS

| | | |
|---|---|---|
| EP | 0 138 757 | 8/1984 |
| WO | WO 2004/085399 | 10/2004 |
| WO | WO 2005/005389 | 1/2005 |

OTHER PUBLICATIONS

U.S. Appl. No. 11/292,358, filed Dec. 1, 2005, Borzilleri et al.
Sonnenberg, E. et al., "Scatter Factor/Hepatocyte Growth Factor and Its Receptor, the c-met Tyrosine Kinase, Can Mediate a Signal Exchange between Mesenchyme and Epithelia during Mouse Development", *The Journal of Cell Biology*, vol. 123, No. 1, pp. 223-235 (Oct. 1993).
Matsumoto, K. et al., "Hepatocyte Growth Factor: Molecular Structure, Roles in Liver Regeneration, and Other Biological Functions", *Critical Reviews in Oncogenesis*, 3(1,2), pp. 27-54 (1992).
Stoker, M. et al., "Scatter factor is a fibroblast-derived modulator of epithelial cell mobility", *Nature*, vol. 327, pp. 239-242 (May 1987).
Montesano, R. et al., "Identification of a Fibroblast-Derived Epithelial Morphogen as Hepatocyte Growth Factor", *Cell*, vol. 67, pp. 901-908 (Nov. 29, 1991).
Stella, M.C. et al., "Molecules in focus—HGF: a multifunctional growth factor controlling cell scattering", *The International Journal of Biochemistry & Cell Biology*, vol. 31, pp. 1357-1362 (1999).
Stuart, K.A. et al. "Hepatocyte growth factor/scatter factor-induced intracellular signalling", *Int. J. of Exp. Path.*, vol. 81, pp. 17-30 (2000).
Bussolino, F. et al., "Hepatocyte Growth Factor Is a Potent Angiogenic Factor Which Stimulates Endothelial Cell Motility and Growth", The *Journal of Cell Biology*, vol. 119, No. 3, pp. 629-641 (Nov. 1992).
Park, M. et al., "Sequence of *MET* protooncogene cDNA has features characteristic of the tyrosine kinase family of growth-factor receptors", *Proc. Natl. Acad. Sci. USA*, vol. 84, pp. 6379-6383 (Sep. 1987).
Bottaro, D.P. et al., "Identification of the Hepatocyte Growth Factor Receptor as the *c-met* Proto-Oncogene Product", *Science*, vol. 251, pp. 802-804 (Feb. 15, 1991).
Furge, K.A. et al., "Met receptor tyrosine kinase: enhanced signaling through adapter proteins", *Oncogene*, vol. 19, pp. 5582-5589 (2000).
Gual, P. et al., "Sustained recruitment of phospholipase C-γ to Gab 1 is required for HGF-induced branching tubulogenesis", *Oncogene*, vol. 19, pp. 1509-1518 (2000).
Schaeper, U. et al., "Coupling of Gab1 to c-Met, Grb2, and Shp2 Mediates Biological Responses", *The Journal of Cell Biology*, vol. 149, No. 7, pp. 1419-1432 (Jun. 26, 2000).
Bardelli, A. et al., "Comcomitant activation of pathways downstream of Grb2 and PI 3-kinase is required for *MET*-mediated metastasis", *Oncogene*, vol. 18, pp. 1139-1146 (1999).

(Continued)

*Primary Examiner*—Zinna N Davis
(74) *Attorney, Agent, or Firm*—Gary D. Greenblatt; Maureen S. Gibbons

(57) ABSTRACT

The invention is directed to compounds having the following Formula I:

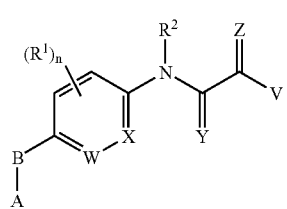

and methods of using them for the treatment of proliferative diseases.

9 Claims, No Drawings

OTHER PUBLICATIONS

Sachs, M. et al., "Essential Role of Gab1 for Signaling by the c-Met Receptor In Vivo", *The Journal of Cell Biology*, vol. 150, No. 6, pp. 1375-1384 (Sep. 18, 2000).

Tanimura, S. et al., "Activation of the 41/43 kDa mitogen-activated protein kinase signaling pathway is required for hepatocyte growth factor-induced cell scattering", *Oncogene*, vol. 17, pp. 57-65 (1998).

Lai, J-F et al., "Involvement of Focal Adhesion Kinase in Hepatocyte Growth Factor-induced Scatter of Madin-Darby Canine Kidney Cells*", *The Journal of Biological Chemistry*, vol. 275, No. 11, pp. 7474-7480 (2000).

Lubensky, I.A. et al., "Hereditary and Sporadic Papillary Renal Carcinomas with *c-met* Mutations Share a Distinct Morphological Phenotype", *American Journal of Pathology*, vol. 155, No. 2, pp. 517-526 (Aug. 1999).

Christiansen, J.G. et al., "A Selective Small Molecule Inhibitor of c-Met Kinase Inhibits c-Met-Dependent Phenotypes in Vitro and Exhibits Cytoreductive Antitumor Activity in Vivo", *Cancer Research*, vol. 63, pp. 7345-7355 (Nov. 1, 2003).

Lee, J-H et al., "A novel germ line juxtamembrane *Met* mutation in human gastric cancer", *Oncogene*, vol. 19, pp. 4947-4953 (2000).

Di Renzo, M.F. et al., "Overexpression and Amplification of the Met/HGF Receptor Gene during the Progression of Colorectal Cancer", *Clinical Cancer Research*, vol. 1, pp. 147-154 (Feb. 1995).

Rong, S. et al., "Met Proto-oncogene Product Is Overexpressed in Tumors of p53-deficient Mice and Tumors of Li-Fraumeni Patients", *Cancer Research*, vol. 55, pp. 1963-1970 (May 1, 1995).

Rong, S. et al., "Met Expression and Sarcoma Tumorigenicity", *Cancer Research*, vol. 53, pp. 5355-5360 (Nov. 15, 1993).

Kenworthy, P. et al., "The presence of scatter factor in patients with metastatic spread to the pleura", *Br. J. Cancer*, vol. 66, pp. 243-247 (1992).

Scarpino, S. et al., "Hepatocyte Growth Factor (HGF) Stimulates Tumour Invasiveness in Papillary Carcinoma of the Thyroid", *Journal of Pathology*, vol. 189, pp. 570-575 (1999).

Soman, N.R. et al., "The *TPR-MET* oncogenic rearrangement is present and expressed in human gastric carcinoma and precursor lesions", *Proc. Natl. Acad. Sci. USA*, vol. 88, pp. 4892-4896 (Jun. 1991).

Camp, R.L. et al., "*Met* Expression Is Associated with Poor Outcome in Patients with Axillary Lymph Node Negative Breast Carcinoma", *Cancer*, vol. 86, No. 11, pp. 2259-2265 (Dec. 1, 1999).

Masuya, D. et al., "The tumour-stromal interaction between intratumoral c-Met and stromal hepatocyte growth factor associated with tumour growth and prognosis in non-small-cell lung cancer patients", *British Journal of Cancer*, vol. 90, pp. 1555-1562 (2004).

Takayama, H. et al., "Diverse tumorigenesis associated with aberrant development in mice overexpressing hepatocyte growth factor/scatter factor", *Proc. Natl. Acad. Sci. USA*, vol. 94, pp. 701-706 (Jan. 1997).

Cooper, C.S. et al., "Amplification and overexpression of the *met* gene in spontaneously transformed NIH3T3 mouse fibroblasts", *The EMBO Journal*, vol. 5, No. 10, pp. 2623-2628 (1986).

Stabile, L.P. et al., "Inhibition of human non-small cell lung tumors by a c-Met antisense/U6 expression plasmid strategy", *Gene Therapy*, vol. 11, pp. 325-335 (2004).

Jiang, W.G. et al., "Reduction of Stromal Fibroblast-induced Mammary Tumor Growth, by Retroviral Ribozyme Transgenes to Hepatocyte Growth Factor/Scatter Factor and its Receptor, c-MET", vol. 9, pp. 4274-4281 (Sep. 15, 2003).

CHEMCATS, Pharma Library Collection, Accession No. 2001:47043. CAS Registry No. 313648-77-0, Publication date: Mar. 15, 2005.

CHEMCATS, Pharma Library Collection, Accession No. 2001:20477 CAS Registry No. 313223-37-9, Publication date: Mar. 15, 2005.

OXALAMIDE DERIVATIVES AS KINASE INHIBITORS

RELATED APPLICATIONS

This application claims priority benefit under Title 35 § 119(e) of U.S. Provisional Application No. 60/673,727, filed Apr. 21, 2005, the contents of which are herein incorporated by reference.

FIELD OF THE INVENTION

This invention relates to compounds that inhibit the protein tyrosine kinase activity of growth factor receptors such as c-Met, thereby making them useful as anti-cancer agents. The pharmaceutical compositions that comprise these compounds are also useful in the treatment of diseases, other than cancer, which are associated with signal transduction pathways operating through growth factor and anti-angiogenesis receptors such as c-Met.

BACKGROUND OF THE INVENTION

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235, 1993; Matsumato et al., *Crit. Rev. Oncog.* 3:27-54, 1992; and Stoker et al., *Nature* 327:239-242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901-908, 1991), and promotion of invasion (Stella et al., *Int. J. Biochem. Cell Biol.* 12:1357-62, 1999 and Stuart et al., *Int. J. Exp. Path.* 81:17-30, 2000), all critical processes underlying metastasis. HGF has also been reported to promote angiogenesis (Bussolino et al., *J. Cell Biol.* 119:629-641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA* 84:6379-83, 1987 and Bottaro et al., *Science* 251:802-4, 1991). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582-9, 2000). These include the p85 subunit of the PI3-kinase, phospholipase Cγ (Gaul et al., *Oncogene* 19:1509-18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149:1419-32, 2000; Bardelli, et al., *Oncogene* 18:1139-46, 1999 and Sachs et al., *J. Cell Biol.* 150:1375-84, 2000). Activation of other signaling molecules has been reported in HGF stimulated cells, most notably Ras, MAP kinases, STATs, ERK-1, -2 and FAK (Tanimura et al., *Oncogene* 17:57-65, 1998; Lai et al., *J. Biol. Chem.* 275:7474-80 2000 and Furge et al., *Oncogene* 19:5582-9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology*, 155:517-26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.*, 63:7345-55, 2003; Lee et al., *Oncogene*, 19:4947-53, 2000 and Direnzo et al., *Clin. Cancer Res.*, 1:147-54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res.* 55:1963-1970, 1995; Rong et al., *Cancer Res.* 53:5355-5360, 1993; Kenworthy et al., *Br. J. Cancer* 66:243-247, 1992 and Scarpino et al. *J Pathology* 189:570-575, 1999). TPR-Met (an activated form similar to BCR/Abl in CML) has been described and identified in human gastric carcinoma (PNAS 88:4892-6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259-65 1999 and Masuya et al., *Br. J. Cancer,* 90:1555-62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS,* 94:701-6, 1997) and an amplified/overexpressed Met spontaneously transforms NIH-3T3 (Cooper et al., *EMBO J.* 5:2623-8, 1986).

Biological agents, such as ribozymes, antibodies and antisense RNA targeting either HGF or Met have been shown to inhibit tumorogenesis (Stabile et al., *Gene Therapy,* 11:325-35, 2004, Jiang et al., *Clin. Cancer Res,* 9:4274-81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

SUMMARY OF THE INVENTION

The present invention is directed to compounds having the following Formula I:

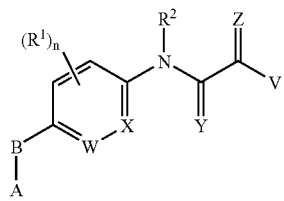

I including pharmaceutically acceptable salts thereof, wherein:
each $R^1$, $R^{12}$, $R^{13}$ and $R^{14}$ are independently H, halogen, cyano, $NO_2$, $OR^3$, $NR^4R^5$, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, substituted heterocyclo, aryalkyl, substituted arylalkyl, heterocycloalkyl, or substituted heterocycloalkyl;
$R^2$ is H, alkyl, substituted alkyl, cycloalkyl, substituted cycloalkyl;
B is O, $NR^6$, S, SO, $SO_2$, or $CR^7R^8$;
W and X are independently CH or N;
Y and Z are independently O or S, but Y and Z cannot both be S;
n is 0 to 4;
V is $-NR^9R^{10}$ or a heterocycle selected from the group consisting of:

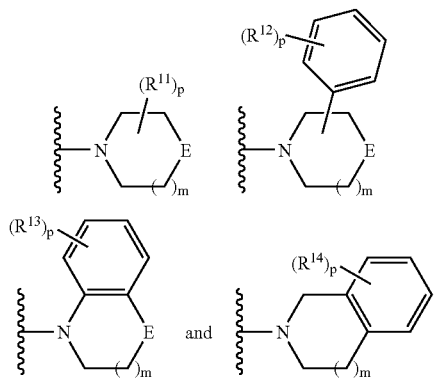

E is $-O-$, $-NR^{15}$, $-CR^{16}R^{17}$, $-S-$, $-SO$, $-SO_2$
m is 0 to 2;
p is 0 to 5;
A is:

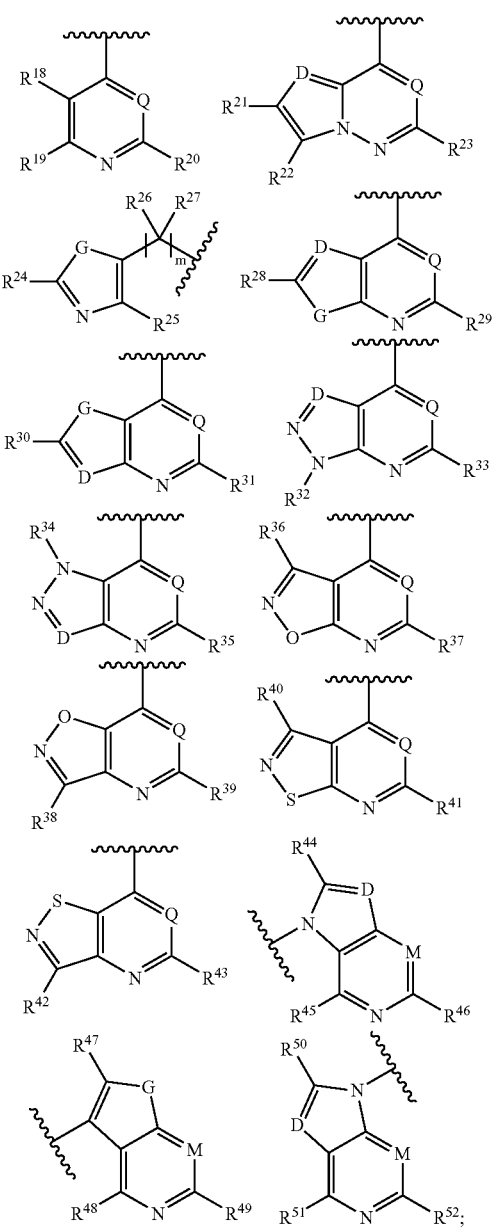

Q is N or $CR^{53}$;
D is N or $CR^{54}$;
G is S, O or $NR^{55}$;
M is N or $CR^{56}$;

with the proviso that if A is

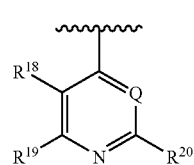

where Q is either N or $CR^{47}$ then $R^9$ or $R^{10}$ cannot be aryl, substituted aryl, heteroaryl, substituted heteroaryl, heterocyclo, or substituted heterocyclo;

$R^3$, $R^4$, $R^5$, $R^6$, $R^9$, $R^{11}$, $R^{15}$, $R^{32}$, $R^{34}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$ and $R^{71}$ are each independently H, alkyl, substituted alkyl, cycloalkyl, substituted cycloalkyl, arylalkyl, substituted arylalkyl, aryl, substituted aryl, heteroaryl, substituted heteroaryl, heterocyclo, substituted heterocyclo, heteroarylalkyl, substituted heteroarylalkyl, heterocycloalkyl, or substituted heterocycloalkyl;

$R^7$ and $R^8$ are independently H, halogen, alkyl, substituted alkyl, cycloalkyl, substituted cycloalkyl, aryl, substituted aryl, heteroaryl, substituted heteroaryl, heterocyclo, substituted heterocyclo or taken together to form an optionally substituted carbocyclic or heterocyclic ring of 3 to 8 atoms;

$R^{16}$ and $R^{17}$ are independently H, alkyl, substituted alkyl, cycloalkyl, substituted cycloalkyl, arylalkyl, substituted arylalkyl, aryl, substituted aryl, heteroaryl, substituted heteroaryl, heterocyclo, substituted heterocyclo, heteroarylalkyl, substituted heteroarylalkyl, heterocycloalkyl, substituted heterocycloalkyl or taken together to form an optionally substituted carbocyclic or heterocyclic ring of 3 to 8 atoms;

$R^{18}$, $R^{19}$, $R^{20}$, $R^{21}$, $R^{22}$, $R^{23}$, $R^{24}$, $R^{25}$, $R^{28}$, $R^{29}$, $R^{30}$, $R^{31}$, $R^{33}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, and $R^{54}$ independently H, halogen, $NO_2$, cyano, $OR^{57}$, $NR^{58}R^{59}$, $CO_2R^{60}$, $C(O)NR^{61}R^{62}$, $SO_2R^{63}$, $SO_2NR^{64}R^{65}$, $NR^{66}SO_2R^{67}$, $NR^{68}C(O)R^{69}$, $NR^{70}CO_2R^{71}$, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclo, or substituted heterocyclo, arylalkyl, substituted arylalkyl, heterocycloalkyl, or substituted heterocycloalkyl;

$R^{26}$ and $R^{27}$ are independently H, F, alkyl, substituted alkyl, cycloalkyl, substituted cycloalkyl, aryl, substituted aryl, heteroaryl, substituted heteroaryl, heterocyclo, substituted heterocyclo or taken together to form an optionally substituted carbocyclic or heterocyclic ring of 3 to 8 atoms;

$R^{53}$ is H or cyano.

The present invention is also directed to pharmaceutical compositions comprising therapeutically effective amounts of a compound of Formula I, or a salt or solvate thereof, together with a pharmaceutically acceptable carrier.

The present invention also provides methods for the treatment of cancer comprising administering to a patient in need thereof a pharmaceutically effective amount of a compound of Formula I or a salt or solvate thereof, optionally including administering to the patient at least one additional anticancer agent.

DETAILED DESCRIPTION OF THE INVENTION

The present invention is directed to compounds of Formula I, as defined above, pharmaceutical compositions employing such compounds, methods of making and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. Preferred alkyl groups have from 1 to 6 carbon atoms. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include the lower alkyl groups, methyl, ethyl, propyl, isopropyl, n-butyl, t-butyl, and isobutyl, as well as pentyl, hexyl, isohexyl, heptyl, 4,4-dimethylpentyl octyl, 2,2,4-trimethylpentyl, nonyl, decyl, undecyl, dodecyl, and the like. Exemplary substituents include but are not limited to one or more of the following groups: alkyl, aryl, halo (such as F, Cl, Br, I), haloalkyl (such as $CCl_3$ or $CF_3$), alkoxy, alkylthio, hydroxy, carboxy(—COOH), alkyloxycarbonyl (—C(O)R), alkylcarbonyloxy (—OCOR), amino (—$NH_2$), carbamoyl (—NHCOOR— or —OCONHR—), urea (—NHCONHR—) or thiol (—SH).

The term "alkenyl" herein alone or as part of another group refers to a hydrocarbon radical straight, branched or cyclic containing from 2 to 12 carbon atoms and at least one carbon to carbon double bond. Alkenyl groups may also be substituted at any available point of attachment. Exemplary substituents for alkenyl groups include those listed above for alkyl groups.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkenyl groups include those listed above for alkyl groups.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl(vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The terms "alkoxy" or "alkylthio" herein alone or as part of another group denote an alkyl group as described above bonded through an oxygen linkage (—O—) or a sulfur linkage (—S—), respectively.

The term "alkoxycarbonyl" herein alone or as part of another group denotes an alkoxy group bonded through a carbonyl group. An alkoxycarbonyl radical is represented by the formula: —C(O)OR, where the R group is a straight or branched $C_{1-6}$ alkyl group, cycloalkyl, aryl, or heteroaryl.

The term "alkylcarbonyl" herein alone or as part of another group refers to an alkyl group bonded through a carbonyl group or —C(O)R.

The term "alkylcarbonyloxy" herein alone or as part of another group denotes an alkylcarbonyl group bonded through an oxygen linkage.

The term "arylalkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=O, 1, 2), or thiol.

The term "amino" herein alone or as part of another group refers to —$NH_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl. carbonyl or carboxyl. These substituents may be further substituted with a carboxylic acid, any of the alkyl or aryl substituents set out herein. In some embodiments, the amino groups are substituted with carboxyl or carbonyl to form N-acyl or N-carbamoyl derivatives.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, selected from the group consisting of halo, alkyl, substituted alkyl, alkenyl, alkynyl, nitro, cyano, oxo(=O), hydroxy, alkoxy, thioalkyl, —$CO_2H$, —C(=O)H, $CO_2$-alkyl, —C(=O)alkyl, keto, =N—OH, =N—O-alkyl, aryl, heteroaryl, heterocyclo, a five or six membered ketal (i.e. 1,3-dioxolane or 1,3-dioxane), —NR'R", —C(=O)NR'R", —$CO_2$NR'R", —C(=O)NR'R", —NR'$CO_2$R", —NR'C(=O)R", —$SO_2$NR'R", and —NR'$SO_2$R", wherein each of R' and R" are independently selected from hydrogen, alkyl, substituted alkyl, and cycloalkyl, or R' and R" together form a heterocyclo or heteroaryl ring.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —$CO_2H$, —C(=O)H, —$CO_2$-alkyl, —C(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —$CO_2$NR'R", —C(=O)NR'R", —NR'$CO_2$R", —$NR^{40}$C(=O)R", —$SO_2$NR'R", and —NR'$SO_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which one of the carbon atoms in the ring is replaced by a heteroatom selected from O, S or N, and in which up to three additional carbon atoms may be replaced by said heteroatoms.

The term "heterocyclic ring" herein alone or as part of another group refers to a stable, saturated, or partially unsaturated monocyclic ring system containing 5 to 7 ring members of carbon atoms and other atoms selected from nitrogen, sulfur and/or oxygen. Preferably, a heterocyclic ring is a 5 or 6-membered monocyclic ring and contains one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclic rings are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclic ring may be attached to the parent structure through a carbon atom or through any heteroatom of the heterocyclyl that results in a stable structure.

The term "heterocyclyl" herein alone or as part of another group as used herein refers to a stable, saturated, or partially unsaturated, monocyclic, bridged monocyclic, bicyclic, and spiro ring system containing carbon atoms and other atoms selected from nitrogen, sulfur and/or oxygen. Preferably, a heterocyclyl is a 5 or 6-membered monocyclic ring or an 8-11 membered bicyclic ring which consists of carbon atoms and contains one, two, or three heteroatoms selected from nitrogen, oxygen and/or sulfur. The term "optionally substituted" as it refers to "heterocyclyl" herein indicates that the heterocyclyl group may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocyclyl groups are isoxazolyl, imidazolinyl, thiazolinyl, imidazolidinyl, pyrrolyl, pyrrolinyl, pyranyl, pyrazinyl, piperidyl, morpholinyl and triazolyl. The heterocyclyl group may be attached to the parent structure through a carbon atom or through any heteroatom of the heterocyclyl that results in a stable structure.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

The term "anticancer" agent includes any known agent that is useful for the treatment of cancer including 17α-Ethinylestradiol, Diethylstilbestrol, Testosterone, Prednisone, Fluoxymesterone, Dromostanolone propionate, Testolactone, Megestrolacetate, Methylprednisolone, Methyl-testosterone, Prednisolone, Triamcinolone, chlorotrianisene, Hydroxyprogesterone, Aminoglutethimide, Estramustine, Medroxyprogesteroneacetate, Leuprolide, Flutamide, Toremifene, Zoladex, matrix metalloproteinase inhibitors, VEGF inhibitors, including as anti-VEGF antibodies such as Avastin, and small molecules such as ZD6474 and SU6668, vatalanib, BAY-43-9006, SU11248, CP-547632, and CEP-7055 are also included. Anti-Her2 antibodies from Genentech (such as Herceptin) may also be utilized. Suitable EGFR inhibitors include gefitinib, erlotinib, and cetuximab. Pan Her inhibitors include canertinib, EKB-569, and GW-572016. Also included are Src inhibitors as well as Casodex® (bicalutamide, Astra Zeneca), Tamoxifen, MEK-1 kinase inhibitors, MAPK kinase inhibitors, PI3 inhibitors, and PDGF inhibitors, such as imatinib. Also included are anti-angiogenic and antivascular agents which, by interrupting blood flow to solid tumors, render cancer cells quiescent by depriving them of nutrition. Castration, which also renders androgen dependent carcinomas non-proliferative, may also be utilized. Also included are IGF1R inhibitors, inhibitors of non-receptor and receptor tyrosine kinases, and inhibitors of integrin signaling. Additional anticancer agents include microtubule-stabilizing agents such as paclitaxel (also known as Taxol®), docetaxel (also known as Taxotere®), 7-O-methylthiomethylpaclitaxel (disclosed in U.S. Pat. No. 5,646,176), 4-desacetyl-4-methylcarbonatepaclitaxel, 3'-tert-butyl-3'-N-tert-butyloxycarbonyl-4-desacetyl-3'-dephenyl-3'-N-debenzoyl-4-O-methoxycarbonyl-paclitaxel (disclosed in U.S. Ser. No. 09/712,352 filed on Nov. 14, 2000), C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo [14.1.0]heptadecane-5,9-dione (disclosed in WO 99/02514), [1S-[1R*,3R*(E),7R*,10S*,11 R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione (disclosed in U.S. Pat. No. 6,262,094) and derivatives thereof; and microtubule-disruptor agents. Also suitable are CDK inhibitors, an antiproliferative cell cycle inhibitor, epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Additional cytotoxic agents include, melphalan, hexamethyl melamine, thiotepa, cytarabin, idatrexate, trimetrexate, dacarbazine, L-asparaginase, camptothecin, topotecan, bicalutamide, flutamide, leuprolide, pyridobenzoindole derivatives, interferons, and interleukins.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species.

The phrase "pharmaceutically acceptable salt(s)", as used herein, unless otherwise indicated, includes salts of acidic or basic groups which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that form nontoxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula I that are acidic in nature, are capable of forming base salts with various pharmacologically acceptable cations. Examples of such salts include the alkali metal or alkaline earth metal salts and particularly, the sodium and potassium salts.

In general, the instant invention comprises compounds of Formula I:

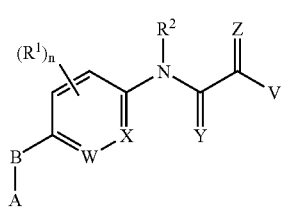

including pharmaceutically acceptable salts thereof, wherein:
each $R^1$, $R^{12}$, $R^{13}$ and $R^{14}$ are independently H, halogen, cyano, $NO_2$, $OR^3$, $NR^4R^5$, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, substituted heterocyclo, arylalkyl, substituted arylalkyl, heterocycloalkyl, or substituted heterocycloalkyl;

$R^2$ is H, alkyl, substituted alkyl, cycloalkyl, substituted cycloalkyl;

B is O, NR$^6$, S, SO, SO$_2$, or CR$^7$R$^8$;
W and X are independently CH or N;
Y and Z are independtly O or S, but Y and Z cannot both be S;
n is 0 to 4;
V is —NR$^9$R$^{10}$ or a heterocycle selected from the group consisiting of:

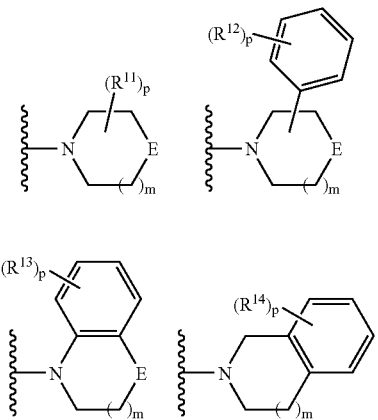

E is —O—, —NR$^{15}$, —CR$^{16}$R$^{17}$, —S—, —SO, or —SO$_2$
m is 0 to 2;
p is 0 to 5;
A is:

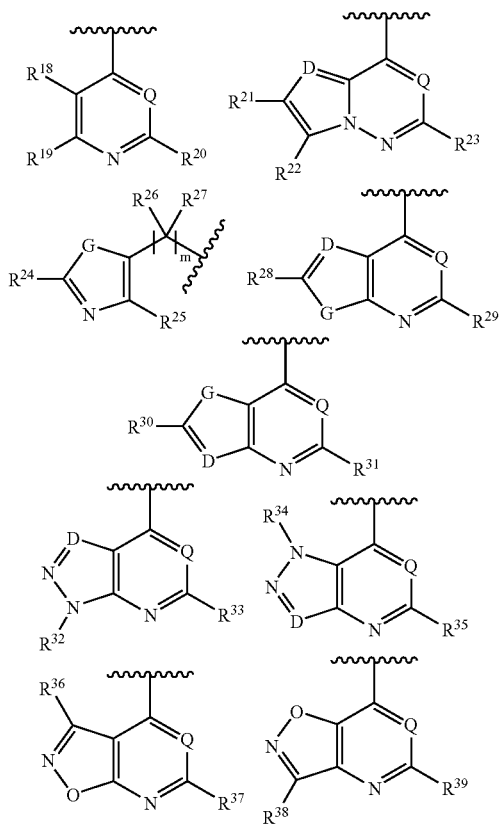

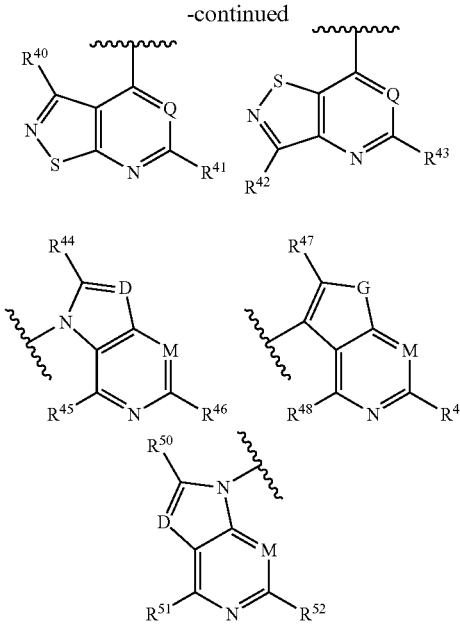

wherein
Q is N or CR$^{53}$;
D is N or CR$^{54}$;
G is S, O or NR$^{55}$;
M is N or CR$^{56}$;

with the proviso that if A is

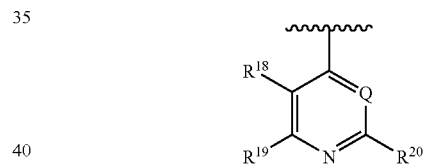

where Q is either N or CR$^{47}$ then R$^9$ or R$^{10}$ cannot be aryl, substituted aryl, heteroaryl, substituted heteroaryl, heterocyclo, or substituted heterocyclo;

R$^3$, R$^4$, R$^5$, R$^6$, R$^9$, R$^{10}$, R$^{11}$, R$^{15}$, R$^{32}$, R$^{34}$, R$^{55}$, R$^{56}$, R$^{57}$, R$^{58}$, R$^{59}$, R$^{60}$, R$^{61}$, R$^{62}$, R$^{63}$, R$^{64}$, R$^{65}$, R$^{66}$, R$^{67}$, R$^{68}$, R$^{69}$, R$^{70}$ and R$^{71}$ are each independently H, alkyl, substituted alkyl, cycloalkyl, substituted cycloalkyl, arylalkyl, substituted arylalkyl, aryl, substituted aryl, heteroaryl, substituted heteroaryl, heterocyclo, substituted heterocyclo, heteroarylalkyl, substituted heteroarylalkyl, heterocycloalkyl, or substituted heterocycloalkyl;

R$^7$ and R$^8$ are independently H, halogen, alkyl, substituted alkyl, cycloalkyl, substituted cycloalkyl, aryl, substituted aryl, heteroaryl, substituted heteroaryl, heterocyclo, substituted heterocyclo or taken together to form an optionally substituted carbocyclic or heterocyclic ring of 3 to 8 atoms;

R$^{16}$ and R$^{17}$ are independently H, alkyl, substituted alkyl, cycloalkyl, substituted cycloalkyl, arylalkyl, substituted arylalkyl, aryl, substituted aryl, heteroaryl, substituted heteroaryl, heterocyclo, substituted heterocyclo, heteroarylalkyl, substituted heteroarylalkyl, heterocycloalkyl, substituted heterocycloalkyl or taken together to form an optionally substituted carbocyclic or heterocyclic ring of 3 to 8 atoms;

$R^{18}$, $R^{19}$, $R^{20}$, $R^{21}$, $R^{22}$, $R^{23}$, $R^{24}$, $R^{25}$, $R^{28}$, $R^{29}$, $R^{30}$, $R^{31}$, $R^{33}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, and $R^{54}$ are independently H, halogen, $NO_2$, cyano, $OR^{57}$, $NR^{58}R^{59}$, $CO_2R^{60}$, $C(O)NR^{61}R^{62}$, $SO_2R^{63}$, $SO_2NR^{64}R^{65}$, $NR^{66}SO_2R^{67}$, $NR^{68}C(O)R^{69}$, $NR^{70}CO_2R^{71}$, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclo, or substituted heterocyclo, arylalkyl, substituted arylalkyl, heterocycloalkyl, or substituted heterocycloalkyl;

$R^{26}$ and $R^{27}$ are independently H, F, alkyl, substituted alkyl, cycloalkyl, substituted cycloalkyl, aryl, substituted aryl, heteroaryl, substituted heteroaryl, heterocyclo, substituted heterocyclo or taken together to form an optionally substituted carbocyclic or heterocyclic ring of 3 to 8 atoms;

$R^{53}$ is H or cyano.

In some embodiments of the present invention, A is pyridine or a pyrrolopyridine, and at least one of Y or Z is O.

In some embodiments of the present invention, Y or Z is S.

In some embodiments of the present invention, V is $NR^9R^{10}$ wherein, preferably, $R^9$ is H and $R^{10}$ is a substituted lower alkyl. The substituent on the lower alkyl may be an aromatic ring or a 5 to 6 membered heteroaromatic ring containing at least one N, O, or S, and is preferably a phenyl group.

The invention also provides methods for treating a proliferative disease via modulation of Met kinase by administering to a patient in need of such treatment an effective amount of a compound of formula I, as defined above.

In another embodiment of the present invention, methods are provided for treating proliferative diseases via modulation of Met kinase by administering to a patient in need of such treatment an effective amount of a compound of formula I, as defined above, in combination (simultaneously or sequentially) with at least one other anti-cancer agent. In a preferred embodiment, the proliferative disease is cancer.

The invention further provides pharmaceutical compositions comprising compounds having formula I together with a pharmaceutically acceptable carrier.

More specifically, the compounds of Formula I are useful in the treatment of a variety of cancers, including, but not limited to, the following:
a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;
b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;
c) hematopoietic tumors of myeloid lineage, including acute and chronic myelogenous leukemias, myelodysplastic syndrome and promyelocytic leukemia;
d) tumors of mesenchymal origin, including fibrosarcoma and rhabdomyosarcoma;
e) tumors of the central and peripheral nervous system, including astrocytoma, neuroblastoma, glioma and schwannomas; and
f) other tumors, including melanoma, seminoma, teratocarcinoma, osteosarcoma, xenoderoma pigmentosum, keratoctanthoma, thyroid follicular cancer and Kaposi's sarcoma.

Due to the key role protein kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

Compounds of Formula I as modulators of apoptosis, will be useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of Formula I may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of Formula I may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of Formula I may also be useful in inhibiting tumor angiogenesis and metastasis.

The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and antimetabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2).

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of Formula I may also be administered sequentially with known anticancer or cytotoxic agents when a combination formulation is inappropriate. The invention is not limited in the sequence of administration; compounds of Formula I may be administered either prior to or after administration of the known anticancer or cytotoxic agent(s).

Certain compounds of Formula I may generally be prepared according to the following Schemes 1 to 3. Tautomers and solvates (e.g., hydrates) of the compounds of Formula I are also within the scope of the present invention. Methods of solvation are generally known in the art. Accordingly, the compounds of the instant invention may be in the free or hydrate form, and may be obtained by methods exemplified by the following schemes below.

In general, the desired fused heterocycles can be prepared using the synthetic routes outlined in Schemes 1-3. The leaving group (Lg), such as a halogen (or triflate) of a heterocycle (A, whereby open positions may be optionally substituted) 1 can be displaced with a substituted phenol 2 to provide ether 3 (Scheme 1). Groups A-Lg can be prepared according to the general procedures outlined in, for example, Hunt, J. T. et al. WO 00/071129; Hunt, J. T. et al. J. Med. Chem. 2004, 47, 4054-4059; Leftheris, K. et al. WO 02/040486; Mastalerz, H. et al. WO 03/042172; Dyckman, A. et al. WO 03/091229; Vite, G. D. et al. WO 04/054514; Salvati, M. E. et al. WO 03/082208; Thibault, C. et al. Org. Lett. 2003, 5, 5023-5025; Zhang, Z. et al. J. Org. Chem. 2002, 67, 2345-2347; Itoh, T. et al. J. Heterocyclic Chem. 1982, 19, 513-517; Tedder, M. E. et al. Bioorg. Med. Chem. Lett. 2004, 14, 3165-3168; Dorn, H. et al. J. Prakt. Chem. 1982, 324, 557; Sanghvi, Y. S. et al. J. Med. Chem. 1989, 32, 945-951; Temple, C. Jr. et al. J. Org. Chem. 1972, 37, 3601-3604; Hurst, J. et al. EP119774; Hurst, J. et al. EP151962; Ward, R. W. et al. EP152910; Luzzio, M. J. et al. WO 01/094353; Marx, M. A. et al. WO 03/000194; Boschelli, D. H. et al. WO 04/048386; He, M. et al. WO 05/021554; Barker, J. M. et al. J. Chem. Res., Synopses 1986, 4, 122-123, the disclosures of which are herein incorporated by reference. Reduction of the nitro group of intermediate 3 with, for example either zinc dust and ammonium chloride or Adam's catalyst (platinum(IV)oxide) under catalytic hydrogenation conditions can furnish the aniline 4. Oxalamide analogues 6 can be prepared by treatment of the appropriately substituted aniline 4 with oxoacetic acid derivatives 5 that are commercially available or easily obtained by methods known in the art (see, e.g. in the presence of a coupling reagent, such as: O-(1H-benzotriazol-1-yl)-N,N,N',N'-tetramethyluronium tetrafluoroborate (TBTU) and a base (i.e., diisopropylethylamine) in DMF (Scheme 1).

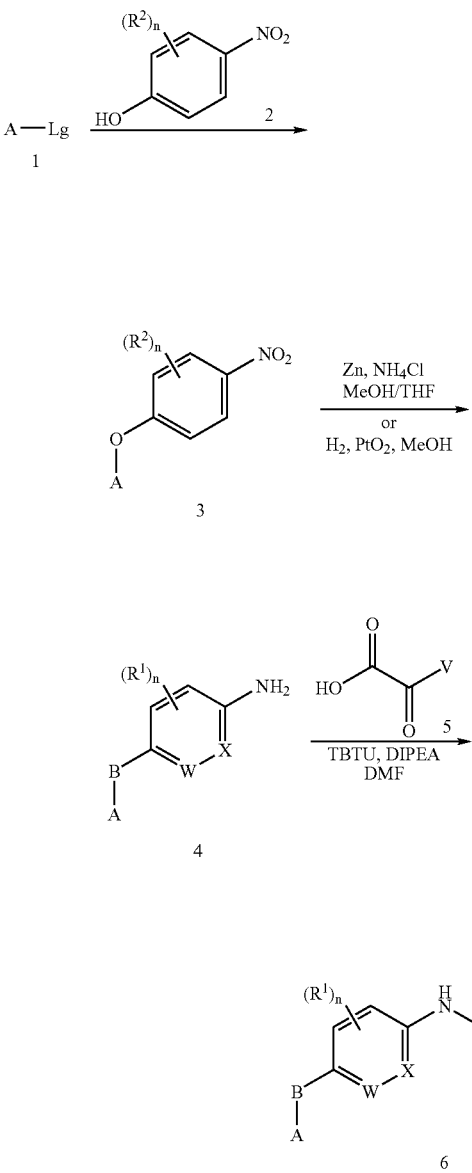

SCHEME 1

The thioxoacetamide derivatives 8 can be prepared directly from intermediate 7 or from compound 10 which is obtained via 9 using chemistry outlined in Scheme 2 (cf. Rus. J. Org. Chem. 2004, 137; J. Prakt. Chem. 1992, 92; J. Prakt. Chem. 1990, 845, the disclosure of which is herein incorporated by reference).

SCHEME 2

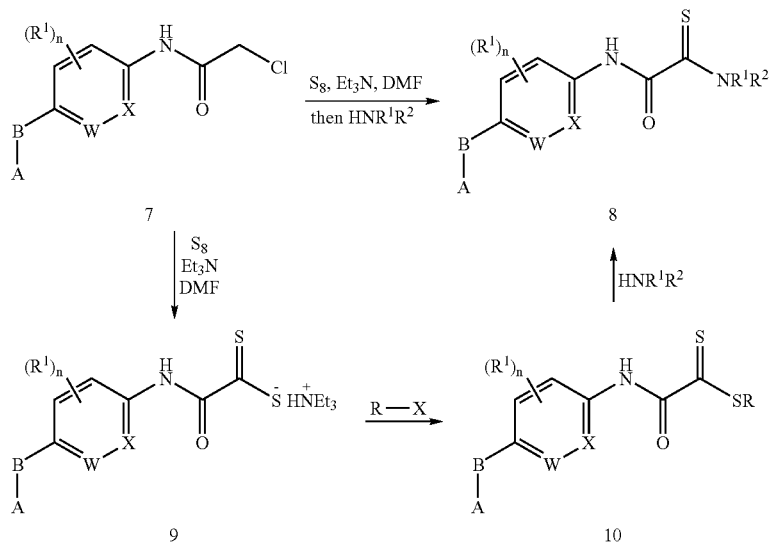

Alternatively, thioxoacetamide derivatives 12 can be prepared from intermediate 11 and compound 4 using similar chemistry (Scheme 3).

SCHEME 3

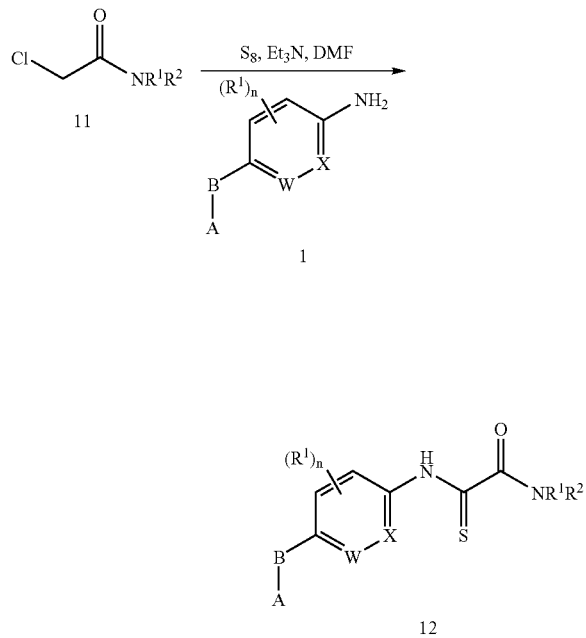

Assays

The pharmacological properties of the compounds of this invention may be confirmed by a number of pharmacological assays. The exemplified pharmacological assays which follow have been carried out with the compounds according to the invention and/or their pharmaceutically acceptable salts.

MET Kinase Assay

| Reagents | Substrate Mix Final Concentration |
|---|---|
| Stock Solution | |
| Tris-HCl, (1M, pH 7.4) | 20 mM |
| $MnCl_2$ (1M) | 1 mM |
| DTT (1M) | 1 mM |
| BSA (100 mg/ml) | 0.1 mg/ml |
| polyGlu$_4$/tyr (10 mg/ml) | 0.1 mg/mL |
| ATP (1 mM) | 1 μM |
| γ-ATP (10 μCi/μl) | 0.2 μCi/ml |
| Buffer | Enzyme mix |
| 20 ul 1M DTT | 4 ul GST/Met enzyme(3.2 mg/ml) = 10 ng/rxn |
| 200 ul 1M Tris-HCL, pH 7.4 | qs 12 ml Buffer |
| 20 ul 100 mg/ml BSA | |
| qs 20 ml $H_2O$ | |

Incubation mixtures employed for the Met kinase assay contain the synthetic substrate polyGlu:Tyr, (4:1), ATP, ATP-γ-$^{33}$P and buffer containing $Mn^{++}$ and/or $Mg^{++}$, DTT, BSA, and Tris buffer. Reactions are incubated for 60 minutes at 27° C. and stopped by the addition of cold trichloroacetic acid (TCA) to a final concentration 4%. TCA precipitates are collected onto GF/C unifilter plates (Packard Instrument Co., Meriden, Conn.) using a Filtermate universal harvester (Packard Instrument Co., Meriden, Conn.) and the filters are quantitated using a TopCount 96-well liquid scintillation counter (Packard Instrument Co., Meriden, Conn.). Dose response curves are generated to determine the concentration required to inhibit 50% of kinase activity ($IC_{50}$). Compounds are dissolved at 10 mM in dimethyl sulfoxide (DMSO) and evaluated at six concentrations, each in quadruplicate. The final concentration of DMSO in the assay is 1%. $IC_{50}$ values are derived by non-linear regression analysis and have a coefficient of variance (SD/mean, n=6)=16%.

Preferred compounds of the invention inhibit the Met kinase enzyme with $IC_{50}$ values between 0.01 to 100 μM. More preferred compounds have $IC_{50}$ values less than 1.0 μM, and most preferably, less than about 0.5 μM.

The following examples and preparations describe the manner and process of making and using the invention and are illustrative rather than limiting. It should be understood that there may be other embodiments which fall within the spirit and scope of the invention as defined by the claims appended hereto.

EXAMPLES

All reactions were carried out with continuous magnetic stirring under an atmosphere of dry nitrogen or argon. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm).

Analytical Reverse Phase (RP) HPLC was performed using a Phenomenex Luna C18 S5 4.6 mm×50 mm column or a YMC S5 ODS 4.6×50 mm column. In each case a 4 min linear gradient (from 100% A: %0 B to 0% A: 100% B) was used with the following mobile phase system: A=90% $H_2O$/MeOH+0.2% $H_3PO_4$; B=90% MeOH/$H_2O$+0.2% $H_3PO_4$ at flow rate=4 mL/min and detection at 220 nm.

Preparative Reverse Phase (RP) HPLC was performed with a linear gradient elution using $H_2O$/MeOH mixtures buffered with 0.1% trifluoroacetic acid and detection at 220 nm on one of the following columns: Shimadzu S5 ODS-VP 20×100 mm (flow rate=9 mL/min), or YMC S10 ODS 50×500 mm (flow rate=50 mL/min), or YMC S10 ODS 30×500 mm (flow rate=20 mL/min).

All final products were characterized by $^1$H NMR, RP HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of δ (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

The following abbreviations are used for commonly used reagents: Boc or BOC: t-butyl carbamate; Fmoc: 9H-fluorenylmethyl carbamate; NMM: N-methylmorpholine; Ms: methanesulfonyl; DIEA or DIPEA: diisopropylethylamine or Hunig's base; NMP: N-methylpyrrolidinone; BOP reagent: benzotriazol-1-yloxytris(trimethylamino)phosphonium hexafluorophosphate; DCC: 1,3-dicyclohexylcarbodiimide; EDCI: 1-(dimethylaminopropyl)-3-ethylcarbodiimide hydrochloride; RT: room temperature; $t_R$: retention time; h: hour(s); min: minute(s); PyBrOP: bromotripyrrolidinophosphonium hexafluorophosphate; TBTU: O-(1H-benzotriazol-1-yl)-N,N,N',N'-tetramethyluronium tetrafluoroborate; DMAP: 4-N,N-dimethylaminopyridine; HOBt: hydroxybenzotriazole; DIBAL-H: diisobutylaluminum hydride; Na(OAc)$_3$BH: sodium triacetoxyborohydride; HOAc: acetic acid; TFA: trifluoroacetic acid; LiHMDS: lithium bis(trimethylsilyl)amide; DMSO: dimethyl sulfoxide; MeCN: acetonitrile; MeOH: methanol; EtOAc: ethyl acetate; DMF: dimethyl formamide; THF: tetrahydrofuran; DCE: 1,2-dichloroethane; $Et_2O$: diethyl ether.

Example 1

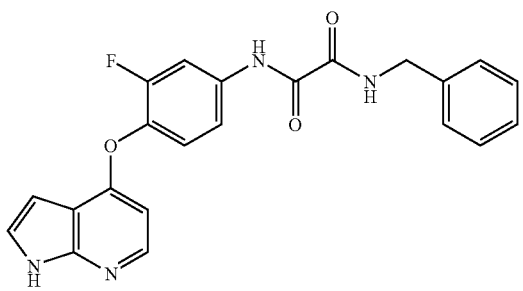

$N^1$-(4-(1H-Pyrrolo[2,3-b]pyridin-4-yloxy)-3-fluorophenyl)-$N^2$-benzyloxalamide

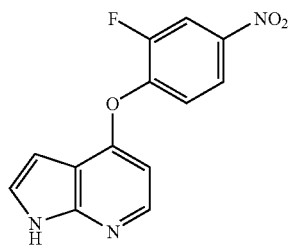

A) 4-(2-Fluoro-4-nitrophenoxy)-1H-pyrrolo[2,3-b]pyridine

A mixture of 4-chloro-1H-pyrrolo[2,3-b]pyridine (Thibault, C. et al. Org. Lett. 2003, 5, 5023; 457 mg, 3.0 mmol, the disclosure of which is hererin incorporated by reference) and 2-fluoro-4-nitrophenol (Aldrich, 706 mg, 4.5 mmol), and N,N-diisopropylethylamine (580 mg, 4.5 mmol) in NMP (3 mL) was heated at 200° C. under microwave irradiation for 1 h. The mixture was diluted with ethyl acetate (150 mL), washed with sat. aq. $KH_2PO_4$ solution, and $Na_2CO_3$ (aq. 1 M), dried over $Na_2SO_4$. The product was purified by flash column chromatography (silica gel, eluting with $CH_2Cl_2$ to 30% EtOAc/$CH_2Cl_2$) to afford a brown solid (350 mg, 43% yield). LC/MS (ESI$^+$) m/z 274 (M+H)$^+$.

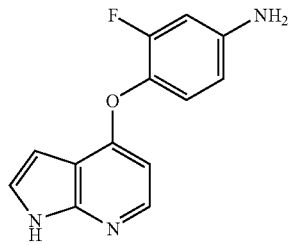

B) 4-(1H-Pyrrolo[2,3-b]pyridin-4-yloxy)-3-fluorobenzenamine

To a suspension of 4-(2-fluoro-4-nitrophenoxy)-1H-pyrrolo[2,3-b]pyridine (300 mg, 1.1 mmol) in THF (5 mL) and methanol (10 mL), were added zinc powder (350 mg, 5.5 mmol) and ammonium chloride (294 mg, 5.5 mmol). The mixture was stirred at rt overnight. The mixture was filtered through a pad of Celite®, rinsed with methanol. The filtrate was concentrated in vacuo and the product was purified by flash column chromatography (silica gel, 1-5% MeOH in $CH_2Cl_2$) to afford the desired product (205 mg, 77% yield) as an off-white solid. LC/MS (ESI$^+$) m/z 244 (M+H)$^+$.

C) $N^1$-(4-(1H-Pyrrolo[2,3-b]pyridin-4-yloxy)-3-fluorophenyl)-$N^2$-benzyloxalamide To 4-(1H-pyrrolo[2,3-b]pyridin-4-yloxy)-3-fluorobenzenamine (30 mg, 0.12 mmol) and 2-(benzylamino)-2-oxoacetic acid (Linton, S. D. et al. *Bioorg. Med. Chem. Lett.* 2004, 14, 2685; 24 mg, 0.136 mmol, the disclosure of which is herein incorporated by reference) in DMF (1 mL) was added DIPEA (63 µL, 0.36 mmol) followed by TBTU (58 mg, 0.18 mmol, Fluka). After stirring at rt for 30 min, the reaction was diluted with water (4 mL) and the product was collected by vacuum filtration. The resulting yellow solid was purified by flash column chromatography on silica gel (EtOAc). The resulting white solid was suspended in 2 mL of dioxane and 0.5 mL of 4 N HCl in dioxane was added. The mixture was concentrated in vacuo and the residue was lyophilized from acetonitrile (1 mL)/water (3 mL) to give the HCl salt of the title compound (34 mg, 64%) as a white solid. $^1$H NMR (DMSO-$d_6$) δ 12.44 (s, 1H), 11.02 (s, 1H), 9.57 (t, 1H, J=6.4 Hz), 8.18 (d, 1H, J=6 Hz), 7.97 (dd, 1H, J=12.8, 2.4 Hz), 7.76 (d, 1H, J=8.8 Hz), 7.48-7.43 (m, 2H), 7.30-7.18 (m, 5H), 6.56 (d, 1H, J=6 Hz), 6.38-6.37 (m, 1H), 4.34 (d, 2H, J=6.4 Hz); MS(ESI$^+$) m/z 405.21 (M+H)$^+$.

Example 2

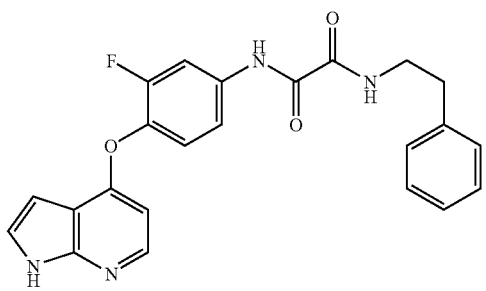

$N^1$-(4-(1H-Pyrrolo[2,3-b]pyridin-4-yloxy)-3-fluorophenyl)-$N^2$-phenethyloxalamide Prepared in a similar manner as described in Step C of Example 1 substituting 2-oxo-2-(phenethylamino)acetic acid for 2-(benzylamino)-2-oxoacetic acid to give the HCl salt of the title compound (55%) as a white solid. $^1$H NMR (DMSO-$d_6$) δ 12.24 (s, 1H), 10.97 (s, 1H), 9.06 (t, 1H, J=6 Hz), 8.14 (d, 1H, J=6 Hz), 7.95 (dd, 1H, J=12.8, 2.4 Hz), 7.74 (d, 1H, J=8.8 HZ), 7.45-7.39 (m, 2H), 7.26-7.13 (m, 5H), 6.49 (d, 1H, J=6 Hz), 6.34 (m, 1H), 3.42-3.37 (m, 2H), 2.78 (t, 2H, J=7.6 Hz); MS(ESI$^+$) m/z 419.26 (M+H)$^+$.

Example 3

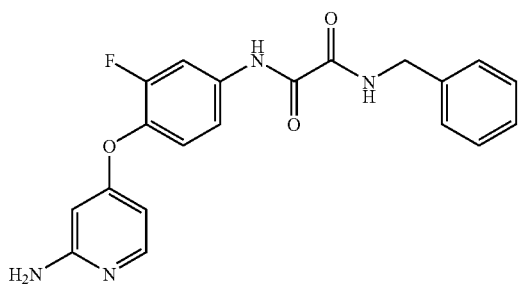

$N^1$-(4-(2-Aminopyridin-4-yloxy)-3-fluorophenyl)-$N^2$-benzyloxalamide

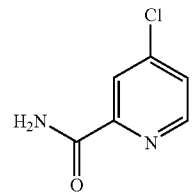

A) 4-Chloropicolinamide

A heterogeneous mixture of 4-chloropicolinic acid (TCI America, 5.4 g, 34.2 mmol, 1.0 eq) and thionyl chloride (30 mL) were heated at 80° C. for 2 h. The reaction mixture was cooled to room temperature and concentrated in vacuo. The residue was treated with an ammonia in MeOH solution (7 N, 45 mL) in an ice bath and the reaction mixture was stirred for 15 minutes. The ice bath was then removed and the reaction was warmed to room temperature and then stirred for 3 h. The reaction mixture was concentrated in vacuo and the residue purified by recrystallization from EtOAc to afford the product (5.14 g, 96%) as a solid. $^1$H NMR (DMSO-$d_6$) δ 8.61-8.63 (m, 1H), 8.21 (m, 1H), 8.03-8.04 (m, 1H), 7.76-7.83 (m, 2H); MS(ESI$^+$) m/z 157 (M+H)$^+$.

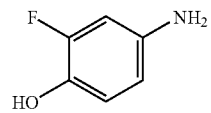

B) 4-Amino-2-fluorophenol

A mixture of platinum oxide (0.010 g) and 2-fluoro-4-nitrophenol (Aldrich, 1.24 g, 7.78 mmol, 1.0 eq) in MeOH (100 mL) was stirred under a $H_2$ atmosphere at 50 psi at room temperature. The reaction mixture was filtered through Celite® and the filtrate concentrated in vacuo to afford the title compound (1.00 g, 100%), as a solid which was used without further purification. $^1$H NMR (DMSO-$d_6$) δ 8.57 (s, 1H), 6.46-6.47 (m, 1H), 6.33-6.46 (m, 1H), 6.19-6.21 (m, 1H), 4.79 (s, 2H); MS(ESI⁺) m/z 128 (M+H)⁺.

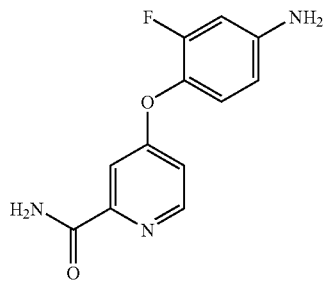

C) 4-(4-Amino-2-fluorophenoxy)picolinamide

A solution of 4-amino-2-fluorophenol (0.81 g, 6.4 mmol, 1.0 eq) in DMF (6.5 mL) was treated with potassium tert-butoxide (0.79 g, 7.1 mmol, 1.1 eq) at room temperature and the reaction mixture was stirred for 1 h. 4-Chloropicolinamide (1.0 g, 6.4 mmol, 1.0 eq) was added and the reaction mixture was heated to 110 IC for 8 h. The reaction was cooled to room temperature and the reaction mixture quenched with water. The resulting heterogeneous solution was filtered and the solid material was washed with water. The solid was triturated with a small amount of MeOH followed by Et₂O. The solid was filtered and dried in vacuo to afford the product (1.3 g, 82%) as a solid. ¹H NMR (DMSO-d₆) δ 8.49-8.50 (m, 1H), 8.12 (br s, 1H), 7.71 (br s, 1H), 7.35-7.36 (m, 1H), 7.14-7.16 (m, 1H), 7.01-7.06 (m, 1H), 6.44-6.47 (m, 2H), 5.53 (s, 2H); MS (ESI⁺) m/z 248 (M+H)⁺.

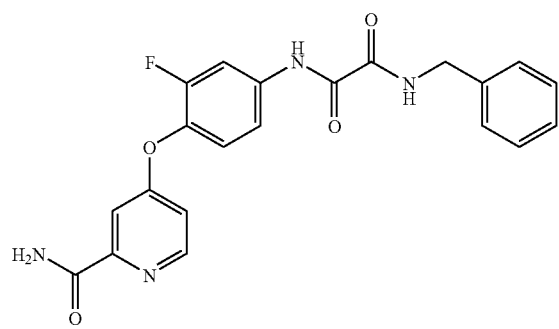

D) 4-(4-(2-(Benzylamino)-2-oxoacetamido)-2-fluorophenoxy)picolinamide

The coupling of 4-(4-amino-2-fluorophenoxy)picolinamide to 2-(benzylamino)-2-oxoacetic acid was carried out in a manner similar to that which is described in Step C of Example 1 to give the title compound (90%) as a tan solid. ¹H NMR (DMSO-d₆) δ 11.08 (s, 1H), 9.63 (t, 1H, J=6 Hz), 8.56 (d, 1H, J=5.6 Hz), 8.15 (br s, 1H), 8.02 (dd, 1H, J=12.8, 2 Hz), 7.82 (d, 1H, J=9.2 Hz), 7.75 (br s, 1H), 7.47 (t, 1H, J=8.8 Hz), 7.39-7.23 (m, 7H), 4.41 (d, 2H, J=6.4 Hz); MS(ESI⁺) m/z 409.22 (M+H)⁺.

E) N¹-(4-(2-Aminopyridin-4-yloxy)-3-fluorophenyl)-N²-benzyloxalamide

To 4-(4-(2-(benzylamino)-2-oxoacetamido)-2-fluorophenoxy)picolinamide (41 mg, 0.10 mmol) in DMF (0.5 mL), water (5 µL, 0.26 mmol), and pyridine (32 µL, 0.39 mmol) was added [bis(trifluoroacetoxy)iodo]benzene (60 mg, 0.14 mmol, Aldrich). After stirring at rt for 2 h, the reaction was diluted with ethyl acetate (20 mL), washed with 10% aqueous lithium chloride solution (2×10 mL) followed by brine (10 mL), dried over anhydrous Na₂SO₄, and concentrated in vacuo. The crude product was purified by flash chromatography on silica gel (EtOAc/0-5% MeOH) to give the title compound as a white solid. The solid was suspended in ethyl acetate (3 mL) and 0.5 mL of 1 N HCl in ether was added. The mixture was concentrated in vacuo and the residue was lyophilized from acetonitrile (1 mL)/water (3 mL) to give the HCl salt of the title compound (25 mg, 60%) as a white solid. ¹H NMR (DMSO-d₆) δ 11.05 (s, 1H), 9.57 (t, 1H, J=6 Hz), 7.96 (dd, 1H, J=12.8, 2 Hz), 7.91 (d, 1H, J=7.2 Hz), 7.81 (br s, 2H), 7.76 (d, 1H, J=8.8 Hz), 7.43 (t, 1H, J=8.8 Hz), 7.29-7.17 (m, 5H), 6.64 (dd, 1H, J=7.2, 2.8 Hz), 6.10 (d, 1H, J=2 Hz), 4.34 (d, 2H, J=6.4 Hz); MS (ESI⁺) m/z 381.24 (M+H)⁺.

Example 4

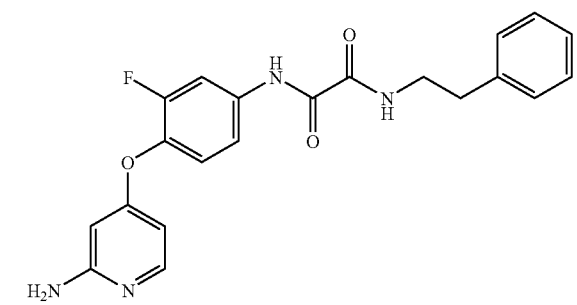

N¹-(4-(2-Aminopyridin-4-yloxy)-3-fluorophenyl)-N²-phenethyloxalamide

¹H NMR (DMSO-d₆) δ 11.00 (s, 1H), 9.06 (t, 1H, J=5.6 Hz), 7.96 (dd, 1H, J=13.2, 2.4 Hz), 7.91 (d, 1H, J=7.2 Hz), 7.79 (br s, 2H), 7.75 (d, 1H, J=9.6 Hz), 7.42 (t, 1H, J=8.8 Hz), 7.26-7.13 (m, 5H), 6.64 (dd, 1H, J=7.2, 2.4 Hz), 6.09 (d, 1H, J=2 Hz), 3.42-3.36 (m, 2H), 2.78 (t, 2H, J=7.6 Hz); MS(ESI⁺) m/z 395.26 (M+H)⁺.

We claim:
1. A compound having the following Formula I:

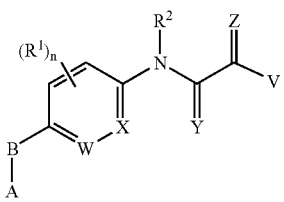

including pharmaceutically acceptable salts thereof, wherein:
each R¹, R¹², R¹³ and R¹⁴ are independently H, halogen, cyano, NO₂, OR³, NR⁴R⁵, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclo, substituted heterocyclo, aryalkyl, substituted arylalkyl, heterocycloalkyl, or substituted heterocycloalkyl;

$R^2$ is H, alkyl, substituted alkyl, cycloalkyl, substituted cycloalkyl;

B is O, $NR^6$, S, SO, $SO_2$, or $CR^7R^8$;

W and X are independently CH or N;

Y and Z are independently O or S, but Y and Z cannot both be S;

n is 0 to 4;

V is —$NR^9R^{10}$ or a heterocycle selected from the group consisting of:

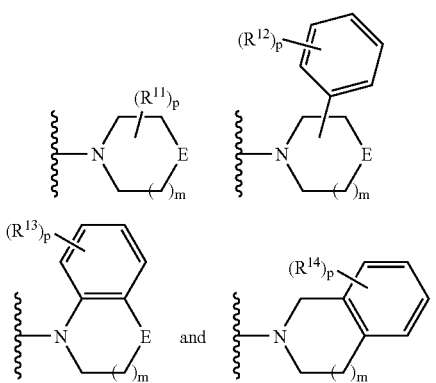

E is —O—, —$NR^{15}$, —$CR^{16}R^{17}$, —S—, —SO, —$SO_2$ m is 0 to 2;

p is 0 to 5;

A is:

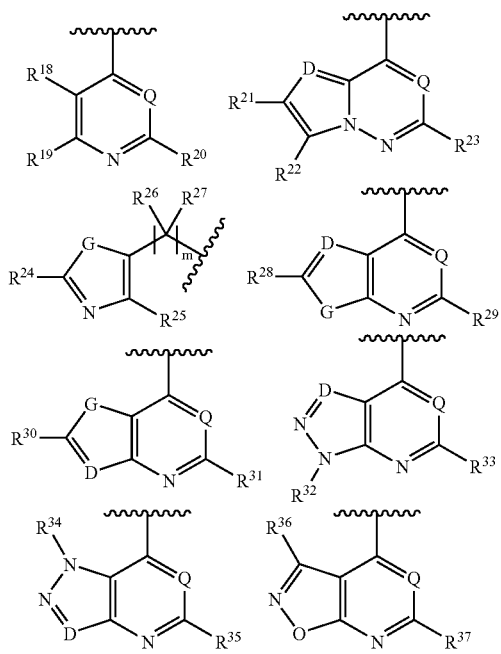

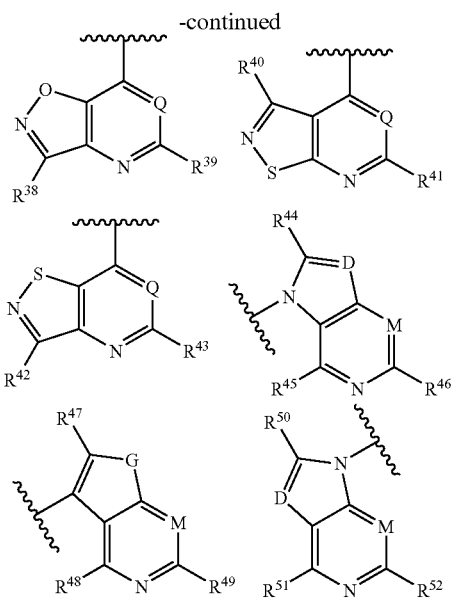

Q is N or $CR^{53}$;
D is N or $CR^{54}$;
G is S, O or $NR^{55}$;
M is N or $CR^{56}$;

with the proviso that if A is

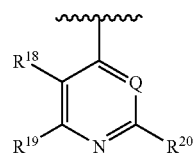

where Q is either N or $CR^{47}$ then $R^9$ or $R^{10}$ cannot be aryl, substituted aryl, heteroaryl, substituted heteroaryl, heterocyclo, or substituted heterocyclo;

$R^3$, $R^4$, $R^5$, $R^6$, $R^9$, $R^{10}$, $R^{11}$, $R^{15}$, $R^{32}$, $R^{34}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$ and $R^{71}$ are each independently H, alkyl, substituted alkyl, cycloalkyl, substituted cycloalkyl, arylalkyl, substituted arylalkyl, aryl, substituted aryl, heteroaryl, substituted heteroaryl, heterocyclo, substituted heterocyclo, heteroarylalkyl, substituted heteroarylalkyl, heterocycloalkyl, or substituted heterocycloalkyl;

$R^7$ and $R^8$ are independently H, halogen, alkyl, substituted alkyl, cycloalkyl, substituted cycloalkyl, aryl, substituted aryl, heteroaryl, substituted heteroaryl, heterocyclo, substituted heterocyclo or taken together to form an optionally substituted carbocyclic or heterocyclic ring of 3 to 8 atoms;

$R^{16}$ and $R^{17}$ are independently H, alkyl, substituted alkyl, cycloalkyl, substituted cycloalkyl, arylalkyl, substituted arylalkyl, aryl, substituted aryl, heteroaryl, substituted heteroaryl, heterocyclo, substituted heterocyclo, heteroarylalkyl, substituted heteroarylalkyl, heterocycloalkyl, substituted heterocycloalkyl or taken together to form an optionally substituted carbocyclic or heterocyclic ring of 3 to 8 atoms;

$R^{18}$ is independently H, halogen, $NO_2$, cyano, $OR^{57}$, $NR^{58}R^{59}$, $CO_2R^{60}$, $C(O)NR^{61}R^{62}$, $SO_2R^{63}$, $SO_2NR^{64}R^{65}$, $NR^{66}SO_2R^{67}$, $NR^{68}C(O)R^{69}$, $NR^{70}CO_2R^{71}$, alkyl, substituted alkyl, cycloalkyl, substituted cycloalkyl, alkenyl, substituted alkenyl, alkynyl, or substituted alkynyl;

$R^{19}$, $R^{20}$, $R^{21}$, $R^{22}$, $R^{23}$, $R^{24}$, $R^{25}$, $R^{28}$, $R^{29}$, $R^{30}$, $R^{31}$, $R^{33}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, $R^{51}$, $R^{52}$, and $R^{54}$ are independently H, halogen, $NO_2$, cyano, $OR^{57}$, $NR^{58}R^{59}$, $C_2R^{60}$, $C(O)NR^{61}R^{62}$, $SO_2R^{63}$, $SO_2NR^{64}R^{65}$, $NR^{66}SO_2R^{67}$, $NR^{68}C(O)R^{69}$, $NR^{70}CO_2R^{71}$, alkyl, substituted alkyl, cycloalkyl, substituted cycloalkyl, alkenyl, substituted alkenyl, alkynyl, substituted alkynyl, aryl, substituted aryl, heteroaryl, substituted heteroaryl, heterocyclo, or substituted heterocyclo, aralkyl, substituted arylalkyl, heterocycloalkyl, or substituted heterocycloalkyl;

$R^{26}$ and $R^{27}$ are independently H, F, alkyl, substituted alkyl, cycloalkyl, substituted cycloalkyl, aryl, substituted aryl, heteroaryl, substituted heteroaryl, heterocyclo, substituted heterocyclo or taken together to form an optionally substituted carbocyclic or heterocyclic ring of 3 to 8 atoms;

$R^{53}$ is H or cyano.

2. The compound according to claim 1 wherein A is pyridine or a pyrrolopyridine.

3. The compound according to claim 1 wherein at least one of Y or Z is O.

4. The compound according to claim 1 wherein Y or Z or S.

5. The compound according to claim 1 wherein V is $-NR^9R^{10}$.

6. The compound according to claim 4 wherein $R^9$ is H and $R^{10}$ is a substituted lower alkyl.

7. The compound according to claim 6 wherein the lower alkyl is substituted with an aromatic or a 5 or 6 membered heteroaromatic ring containing at least one N, O, or S.

8. A compound selected from the group consisting of:
N1-(4-(1H-Pyrrolo[2,3-b]pyridin-4-yloxy)-3-fluorophenyl)-N-2-benzyloxalamide;
N1-(4-(1H-Pyrrolo[2,3-b]pyridin-4-yloxy)-3-fluorophenyl)-N-2-phenethyloxalamide;
N1-(4-(2-Aminopyridin-4-yloxy)-3-fluorophenyl)-N-2-benzyloxalamide; and
N1-(4-(2-Aminopyridin-4-yloxy)-3-fluorophenyl)-N-2-phenethyloxalamide.

9. A pharmaceutical composition comprising a compound according to claim 1 in a pharmaceutically acceptable carrier.

* * * * *

UNITED STATES PATENT AND TRADEMARK OFFICE
CERTIFICATE OF CORRECTION

PATENT NO. : 7,470,693 B2
APPLICATION NO. : 11/406795
DATED : December 30, 2008
INVENTOR(S) : Borzilleri et al.

It is certified that error appears in the above-identified patent and that said Letters Patent is hereby corrected as shown below:

<u>In Column 30, Claim 4,</u>
"4. The compound according to claim 1 wherein Y or Z or S." should read:
-- 4. The compound according to claim 1 where Y or Z is S. --

<u>In Column 30, Claim 6,</u>
"6. The compound according to claim 4 wherein $R^9$ is H and $R^{10}$ is a substituted lower alkyl." should read:
-- 6. The compound according to claim 5 wherein $R^9$ is H and $R^{10}$ is a substituted lower alkyl. --

<u>In Column 30, Claim 8,</u>
"8. A compound selected from the group consisting of:
N1-(4-(1H-Pyrrolo[2,3-b]pyridin-4-yloxy)-3-fluorophenyl)-N-2-benzyloxalamide;
N1-(4-(1H-Pyrrolo[2,3-b]pyridin-4-yloxy)-3-fluorophenyl)-N-2-phenethyloxalamide;
N1-(4-(2-Aminopyridin-4-yloxy)-3-fluorophenyl)-N-2-benzyloxalamide; and
N1-(4-(2-Aminopyridin-4-yloxy)-3-fluorophenyl)-N-2-phenethyloxalamide." should read:
-- 8. A compound selected from the group consisting of:
N1-(4-(1H-Pyrrolo[2,3-b]pyridin-4-yloxy)-3-fluorophenyl)-N2-benzyloxalamide;
N1-(4-(1H-Pyrrolo[2,3-b]pyridin-4-yloxy)-3-fluorophenyl)-N2-phenethyloxalamide;
N1-(4-(2-Aminopyridin-4-yloxy)-3-fluorophenyl)-N2-benzyloxalamide; and
N1-(4-(2-Aminopyridin-4-yloxy)-3-fluorophenyl)-N2-phenethyloxalamide. --

Signed and Sealed this

Third Day of March, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,470,693 B2  Page 1 of 1
APPLICATION NO. : 11/406795
DATED : December 30, 2008
INVENTOR(S) : Borzilleri et al.

It is certified that error appears in the above-identified patent and that said Letters Patent is hereby corrected as shown below:

In Column 30, Claim 4, line 3,
"4. The compound according to claim 1 wherein Y or Z or S." should read:
-- 4. The compound according to claim 1 where Y or Z is S. --

In Column 30, Claim 6, lines 6 and 7,
"6. The compound according to claim 4 wherein $R^9$ is H and $R^{10}$ is a substituted lower alkyl." should read:
-- 6. The compound according to claim 5 wherein $R^9$ is H and $R^{10}$ is a substituted lower alkyl. --

In Column 30, Claim 8, lines 11-19,
"8. A compound selected from the group consisting of:
N1-(4-(1H-Pyrrolo[2,3-b]pyridin-4-yloxy)-3-fluorophenyl)-N-2-benzyloxalamide;
N1-(4-(1H-Pyrrolo[2,3-b]pyridin-4-yloxy)-3-fluorophenyl)-N-2-phenethyloxalamide;
N1-(4-(2-Aminopyridin-4-yloxy)-3-fluorophenyl)-N-2-benzyloxalamide; and
N1-(4-(2-Aminopyridin-4-yloxy)-3-fluorophenyl)-N-2-phenethyloxalamide." should read:
-- 8. A compound selected from the group consisting of:
N1-(4-(1H-Pyrrolo[2,3-b]pyridin-4-yloxy)-3-fluorophenyl)-N2-benzyloxalamide;
N1-(4-(1H-Pyrrolo[2,3-b]pyridin-4-yloxy)-3-fluorophenyl)-N2-phenethyloxalamide;
N1-(4-(2-Aminopyridin-4-yloxy)-3-fluorophenyl)-N2-benzyloxalamide; and
N1-(4-(2-Aminopyridin-4-yloxy)-3-fluorophenyl)-N2-phenethyloxalamide. --

This certificate supersedes the Certificate of Correction issued March 3, 2009.

Signed and Sealed this

Thirty-first Day of March, 2009

JOHN DOLL
*Acting Director of the United States Patent and Trademark Office*